US00PP24351P3

(12) United States Plant Patent
Kristensen

(10) Patent No.: US PP24,351 P3
(45) Date of Patent: Mar. 25, 2014

(54) *OSTEOSPERMUM* PLANT NAMED 'SAKOST8433'

(50) Latin Name: *Osteospermum hybrida*
Varietal Denomination: SAKOST8433

(75) Inventor: Niels G. Kristensen, Grauballe (DK)

(73) Assignee: Sakata Ornamentals Europe A/S, Marslev (DK)

( * ) Notice: Subject to any disclaimer, the term of this patent is extended or adjusted under 35 U.S.C. 154(b) by 127 days.

(21) Appl. No.: 13/385,110

(22) Filed: Feb. 2, 2012

(65) Prior Publication Data

US 2013/0205459 P1 Aug. 8, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — June Hwu
(74) *Attorney, Agent, or Firm* — James M. Weatherly; Cochran Freund & Young LLC

(57) ABSTRACT

A new *Osteospermum* plant particularly distinguished by having a reddish-purple to orange flower color, large flower size and a compact plant habit is disclosed.

1 Drawing Sheet

Genus and species: *Osteospermum hybrida.*
Variety denomination: 'SAKOST8433'.

BACKGROUND OF THE NEW PLANT

The present invention comprises a new and distinct variety of *Osteospermum*, botanically known as *Osteospermum hybrida*, and hereinafter referred to by the variety name 'SAKOST8433'. 'SAKOST8433' originated from a hybridization of *Osteospermum* proprietary breeding line '206065' and the commercial hybrid *Osteospermum* line 'SAKOST8077' (U.S. Plant Pat. No. 22,628) in Marslev, Denmark. The female parent, '206065' has a dark yellow to bronze flower color, brown center and a fairly compact plant habit. The male parent, 'SAKOST8077', has a red to bronze flower color with a brown center and a semi-erect plant habit.

In June 2007, the two *Osteospermum* lines '206065' and 'SAKOST8077' were crossed and seeds were obtained. The seeds were sown and 108 plants were grown in pots for evaluation. Out of 108 $F_1$ lines, one plant, named plant number 40, was selected which had reddish-purple to orange flowers, a large flower size and a compact plant habit.

In February 2008, plant number 40 was vegetatively propagated by cuttings and re-evaluated in an open field and a greenhouse. Plant number 40 was given the breeder code number 'OST208040' and the stability of the distinct characteristics of this variety was confirmed.

In May 2008, plants from 'OST208040' were evaluated again in pots and in an open field. 'OST208040' was renamed 'SAKOST8433' and was found to reproduce true to type in successive generations of asexual propagation from vegetative cuttings.

SUMMARY

The following are the most outstanding and distinguishing characteristics of this new variety when grown under normal horticultural practices in Salinas, Calif.

1. Reddish purple to orange flower color;
2. Large flower size; and
3. Compact plant habit.

DESCRIPTION OF THE PHOTOGRAPHS

This new *Osteospermum* plant is illustrated by the accompanying photographs which show the plant's overall plant habit including form, foliage, and flowers. The photographs are of a plant grown four months from transplant (five months from sticking) into 4-inch pots from rooted cuttings in Salinas, Calif. under greenhouse conditions in the spring of 2011. The colors shown are as true as can be reasonably obtained by conventional photographic procedures.

DESCRIPTION OF THE NEW VARIETY

Figure 1:
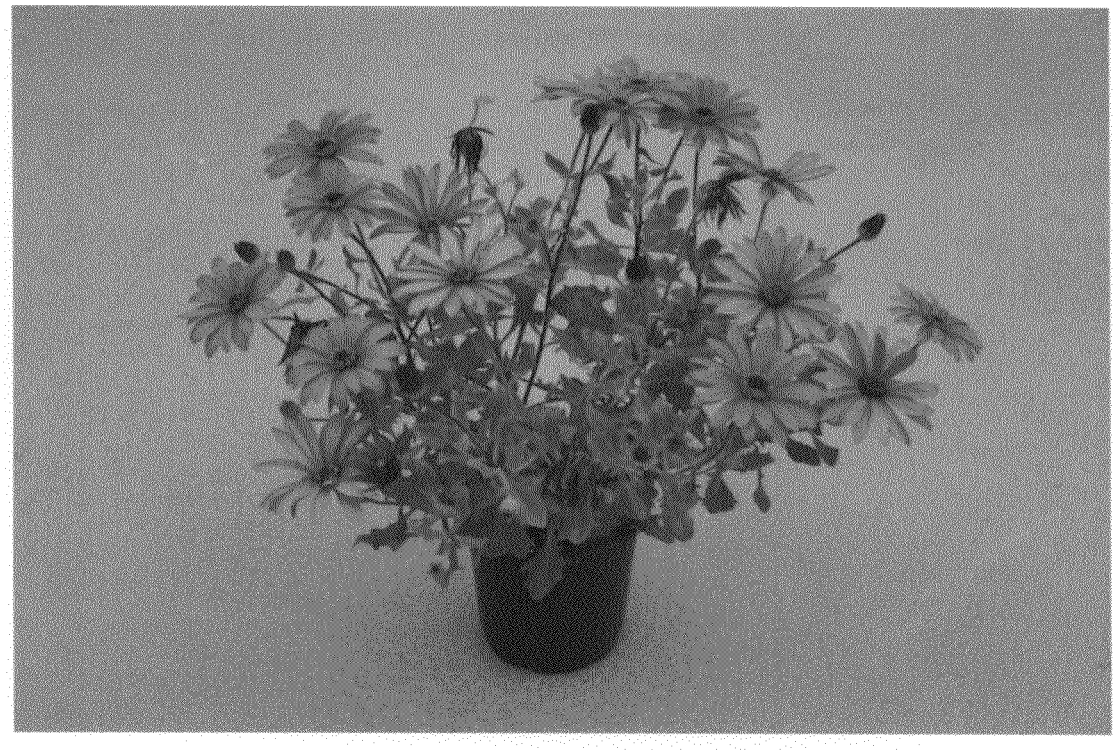
FIG. 1 shows the overall plant habit of the plant grown in a pot.
Figure 2:
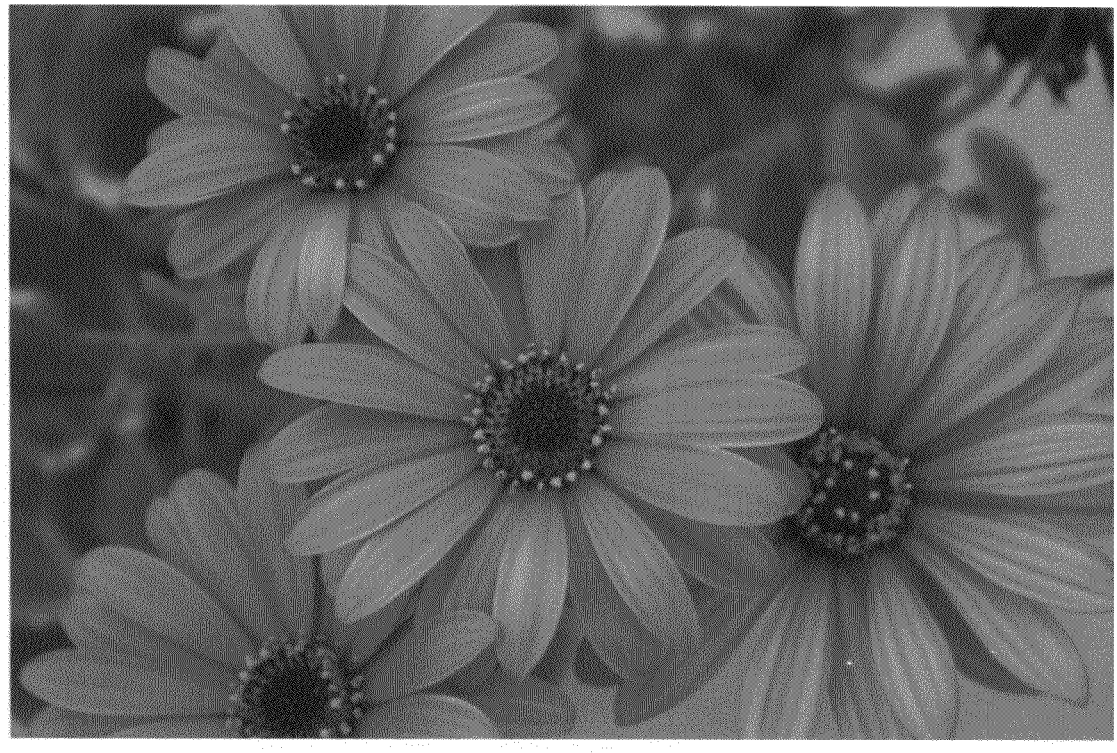
FIG. 2 shows the mature inflorescence of the plant.

The following detailed descriptions set forth the distinctive characteristics of 'SAKOST8433'. The data which define these characteristics were collected from asexual reproductions from vegetative cuttings carried out in Salinas, Calif. Data was collected on plants grown approximately four months from transplant (five months from sticking) into 4-inch pots under greenhouse conditions in Salinas, Calif. in the winter of 2011. Color references are to The R.H.S. Colour Chart of The Royal Horticultural Society of London (R.H.S.), $4^{th}$ edition.

Classification:

*Family.*—Compositae.
*Botanical.—Osteospermum hybrida.*
*Common.—Osteospermum*, Cape Daisy, South African Daisy.
*Designation.*—'SAKOST8433'.

Parentage:

*Female parent.*—The proprietary *Osteospermum* line '206065' (unpatented).
*Male parent.*—The *Osteospermum* line 'SAKOST8077' (U.S. Plant Pat. No. 22,628).

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW, a liquid rooting concentrate for root inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height they are pinched back to 5 to 6 leaves to promote branching. Spring and summer daytime high temperatures in Salinas, Calif. where the data was collected, range from 16° C. to 25° C.

*Time to bloom from propagation.*—Approximately four weeks when rooted vegetative cuttings are transferred to a 4-inch diameter pot. Flowering season is all year in the United States when grown in a greenhouse, otherwise, it is spring to fall. Vernalization is not required to induce flowering.

Plant description:

*Habit.*—Compact.
*Life cycle.*—Annual.
*Form.*—Compact.
*Height (from soil line to first node).*—0.5 cm.
*Height (from soil line to top of foliage).*—20.0 cm to 21.0 cm.
*Width.*—33.0 cm to 34.0 cm.

Stems:

*General.*—Multiple; circular in cross-section.
*Stem length (total).*—10.0 cm to 11.0 cm.
*Diameter.*—0.2 cm.
*Internode length.*—1.5 cm.
*Color.*—RHS 144B (Yellow-green) with RHS 187A (Greyed-purple) anthocyanin.
*Pubescence.*—Moderate. Color: RHS N155A (White). Shape: Short, hair-like fibers.
*Anthocyanin color.*—Slight, RHS 187A (Greyed-purple).

Branches:

*General.*—Circular in cross-section.
*Number of main branches.*—One.
*Total number of branches.*—Six.
*Length.*—8.0 cm; approximately 1.0 cm from soil line to first node, 2.0 cm between first and second nodes.
*Diameter.*—0.4 cm.
*Internode length.*—2.0 cm.
*Color.*—RHS 144B (Yellow-green) with RHS 187A (Greyed-purple) anthocyanin.
*Pubescence.*—Moderate.
*Pubescence shape.*—Short, hair-like fibers.
*Pubescence color.*—RHS N155A (White).
*Anthocyanin color.*—RHS 187A (Greyed-purple).

Leaves:

*Arrangement.*—Alternate.
*Shape.*—Oblanceolate.
*Apex.*—Acute.
*Base.*—Attenuate.
*Margin.*—Serrate.
*Venation.*—Pinnate.
*Surface (both surfaces).*—Dull.
*Surface pubescence (both surfaces).*—Slight, mainly around edge.
*Surface pubescence color.*—RHS N155A (White).
*Attachment.*—Decurrant.
*Length.*—7.0 cm.
*Width.*—2.0 cm.
*Thickness.*—Less than 0.1 cm.
*Color.*—Upper surface: RHS 143A (Green). Lower surface: RHS 143B (Green).
*Venation color.*—Upper surface: RHS 143C (Green). Lower surface: RHS 143C (Green).

Inflorescence:

*Number per plant.*—17.
*Type.*—Capitulum (head); disc florets are perfect and ray florets are carpellate.
*Flowering habit.*—Determinate.
*Lastingness of inflorescences.*—3 to 4 days.
*Fragrance.*—Absent.
*Seed production.*—None observed.
*Diameter.*—7.0 cm to 8.0 cm.
*Depth.*—0.5 cm.
*Ray floret number.*—20 to 26 per inflorescence.
*Disc diameter.*—1.5 cm.
*Disc floret number.*—80 to 100 per inflorescence.
*Peduncle length.*—6.0 cm from inflorescence to first node.
*Peduncle diameter.*—0.2 cm.
*Peduncle color.*—RHS 144B (Yellow-green) with RHS 187A (Greyed-purple) anthocyanin.
*Peduncle texture.*—Dull; slight pubescence.
*Phyllaries.*—Arrangement: 26 per inflorescence; free; arranged symmetrically. Length: 1.0 cm. Width: 0.2 cm. Apex: Acute. Margin: Entire. Shape: Linear; acute. Color: Upper surface: RHS 144C (Yellow-green). Lower surface: RHS 144B (Yellow-green).

Ray florets (ligules):

*Corolla.*—One ray per ray floret; only the outer row of florets are the ray florets.
*Number of ray florets.*—18 to 24 per inflorescence.
*Length.*—3.7 cm.
*Width.*—0.9 cm.
*Shape.*—Lanceolate.
*Apex.*—Acute.
*Margin.*—Entire.
*Base.*—Fused.
*Color.*—Upper surface: Stripes of RHS 61A (Red-purple) and RHS 61C (Red-purple) with RHS 26A (Orange) from the center to the tip; ray florets are darker at the base and change from light red-purple at the base to orange at the tip. Lower surface: Stripes of RHS 187A (Greyed-purple), RHS 183A (Greyed-purple) and RHS 22B (Yellow-orange).
*Pubescence.*—Glabrous.

Disc florets:

*Color.*—RHS N187A (Greyed-purple).
*Shape.*—Tubular.
*Apex.*—Pointed.
*Texture.*—Dull, pubescent.
*Size.*—Length: 0.6 cm. Width: 0.1 cm.

Reproductive organs:

*Ovary.*—Superior.
*Pistil form.*—One style with two stigma branches.
*Pistil length.*—0.5 cm.
*Stigma color.*—RHS N187A (Greyed-purple).
*Style color.*—RHS 187D (Greyed-purple).
*Stamens.*—5; fused into a single tube.

*Anther color.*—RHS 187A (Greyed-purple).
*Pollen color.*—RHS 17A (Yellow-orange).
*Filament color.*—RHS 155A (White).

Disease and insect resistance: No known resistance or susceptibility.

COMPARISON WITH PARENTAL LINES AND KNOWN VARIETY

'SAKOST8433' is a distinct variety of *Osteospermum* owing to its reddish-purple to orange flowers, a large flower size and a compact plant habit. 'SAKOST8433' is distinguished from its parent as described in Table 1 (color references are to The Royal Horticultural Society Colour Chart, 4$^{th}$ edition):

TABLE 1

Comparison with Parental Lines

| Characteristic | 'SAKOST8433' | Male Parent 'SAKOST8077' | Female parent '206065' |
|---|---|---|---|
| Ray floret (ligule) color, upper surface: | Stripes of RHS 61A (Red-purple) and RHS 61C (Red-purple) with RHS 26A (Orange) from the center to the tip. Ray florets are darker at base and go from reddish purple to orange at the tip. | RHS 26A (Orange) | Dark yellow to bronze |
| Plant habit | Compact | Semi-erect | Compact |

'SAKOST8433' is a distinct variety of *Osteospermum* owing to its reddish purple to orange flower color, large flower size and compact plant habit. 'SAKOST8433' is most similar to the *Osteospermum* plant named 'SAKOST8077' (U.S. application Ser. No. 12/657,835). Differences between the two varieties are described in Table 2 (color references are to The Royal Horticultural Society Colour Chart, 4$^{th}$ edition):

TABLE 2

Comparison with Similar Variety

| Characteristic | 'SAKOST8433' | 'SAKOST8077' |
|---|---|---|
| Ray floret (ligule) color, upper surface: | Stripes of RHS 61A (Red-purple) and RHS 61C (Red-purple) with RHS 26A (Orange) from center to tip. Ray florets are darker at base and go from reddish purple to orange at the tip. | RHS 26A (Orange) |
| Plant habit | Compact | Semi-erect |
| Flower Size | Large | Small-medium |

I claim:

1. A new and distinct variety of *Osteospermum* plant as shown and described herein.

* * * * *